(12) United States Patent
Robertson et al.

(10) Patent No.: US 7,481,098 B2
(45) Date of Patent: Jan. 27, 2009

(54) METHOD OF DETERMINING DEPTH OF INTERGRANULAR ATTACK (IGA) FOR A METAL PART

(75) Inventors: John M. Robertson, Andover, CT (US); Richard B. Ringler, Middletown, CT (US); Stephen M. Kurpaska, Newington, CT (US)

(73) Assignee: United Technologies Corporation, Hartford, CT (US)

( * ) Notice: Subject to any disclaimer, the term of this patent is extended or adjusted under 35 U.S.C. 154(b) by 38 days.

(21) Appl. No.: 11/820,162

(22) Filed: Jun. 18, 2007

(65) Prior Publication Data

US 2008/0308958 A1 Dec. 18, 2008

(51) Int. Cl.
*G01N 19/08* (2006.01)

(52) U.S. Cl. ........................................................ 73/104

(58) Field of Classification Search ................... 73/104, 73/105; 264/40.1, 300
See application file for complete search history.

(56) References Cited

U.S. PATENT DOCUMENTS

| | | | | |
|---|---|---|---|---|
| 2,984,101 | A | * | 5/1961 | Minor et al. ................... 73/104 |
| 3,814,695 | A | * | 6/1974 | Molina ................... 252/301.19 |
| 3,862,047 | A | * | 1/1975 | Weltman et al. .......... 252/62.52 |
| 4,008,844 | A | | 2/1977 | Duvall et al. |
| 4,198,362 | A | * | 4/1980 | Ticker et al. ................ 264/40.1 |
| 5,610,326 | A | * | 3/1997 | Leost ............................ 73/105 |
| 5,806,751 | A | | 9/1998 | Schaefer et al. |
| 6,367,686 | B1 | | 4/2002 | Abriles et al. |
| 6,503,349 | B2 | | 1/2003 | Pietruska et al. |
| 6,530,971 | B1 | | 3/2003 | Cohen et al. |
| 7,156,280 | B1 | | 1/2007 | Jiang et al. |

| | | | |
|---|---|---|---|
| 2006/0248718 | A1 | 11/2006 | Szela et al. |

FOREIGN PATENT DOCUMENTS

| | | | | |
|---|---|---|---|---|
| JP | 59079832 | A | * | 5/1984 |
| JP | 02170010 | A | * | 6/1990 |
| JP | 03221831 | A | * | 9/1991 |
| JP | 04012242 | A | * | 1/1992 |
| JP | 05045266 | A | * | 2/1993 |

OTHER PUBLICATIONS

Electron Microscopy Sciences—Technical Data Sheets: "Replicating Sheet—Cellulose Acetate Film", from http://www.emsdiasum.com/microscopy/technical/datasheet/50420.aspx, visited Jan. 18, 2007 (1 page).

(Continued)

*Primary Examiner*—John Fitzgerald
(74) *Attorney, Agent, or Firm*—Kinney & Lange, P.A.

(57) ABSTRACT

A method of determining a depth of intergranular attack (IGA) on a surface of a metal part includes applying a replicating material on a second surface of the part that is essentially perpendicular to and intersects with the surface of interest. The replicating material is used to create an inverted replica of the microstructure of the second surface. Lengths of the cracks replicated on the replicating material are measured in order to determine the depth of intergranular attack on the surface of the part. In some embodiments, a fixture device may be temporarily attached to the metal part to maintain an edge of the second surface.

32 Claims, 5 Drawing Sheets

OTHER PUBLICATIONS

Electron Microscopy Sciences: "Material Science and Metrology", from http://www.emsdiasum.com/microscopy/products/materials/replicating.aspx, visited May 30, 2007 (2 pages).

Ted Pella, Inc.: "Replication Materials", from http://www.tedpella.com/replicat_html/44840.htm, visited Feb. 28, 2007 (2 pages).

"Acetate Cellulose Replicating Film", PELCO® Technical Notes, Replicating Sheet—link from http://www.tedpella.com/replicat_html/44840.htm, visited Feb. 28, 2007 (2 pages).

SPI Supplies: "SPI Replicating Tapes and Sheets", from http://www.2spi.com/catalog/submat/cellulose-acetate-replicating-tape-sheets.shtml, visited Feb. 28, 2007 (3 pages).

Material Safety Data Sheets for Collodion, U.S.P., from http://jtbaker.com/msds/englishhtml/c5060.htm, visited May 23, 2007 (9 pages).

* cited by examiner

_US 7,481,098 B2_

METHOD OF DETERMINING DEPTH OF INTERGRANULAR ATTACK (IGA) FOR A METAL PART

BACKGROUND

The present invention relates to a method of replicating a microstructure of a metal part. More particularly, the present invention relates to a method of determining a depth of intergranular attack (IGA) on a surface of a metal part, such as those used in an aircraft engine.

Metal parts may be prone to developing cracks, especially when exposed to extreme conditions. For example, a gas turbine engine operates at extreme temperatures and pressures. As a result, parts within the engine, such as blades and vanes, may crack. A repair process for a blade or vane within an assembly includes filling the cracks with liquid metal and then heat treating the blade or vane assembly. Prior to filling the cracks with liquid metal, the blade or vane assembly may commonly be cleaned with an acid such as hydrofluoric acid. The acid may result in a surface attack of the assembly. The surface attack may be so destructive, in some cases, that it is not worthwhile to repair the original crack or cracks in the assembly. As such, it is necessary to determine the extent of the surface attack and the depth of the intergranular attack, before repairing a cracked blade or vane assembly.

A small portion or sample of the assembly may be cut-out and placed under a microscope in order to view the microstructure of the sample and determine a depth of intergranular attack in the assembly. However, this technique requires that the sample be rewelded to the assembly and that the assembly then be heat treated. Alternatively, a replacement portion may be welded into the assembly, but the same steps must be followed in either case. This technique is not only destructive to the assembly, but is also time consuming. There is a need for a non-destructive method of accurately determining the depth of intergranular attack in a metal alloy part.

SUMMARY

The present invention relates to a method of determining a depth of intergranular attack (IGA) on a surface of a metal part. The method includes applying a replicating material on a second surface of the part that is essentially perpendicular to and intersects with the surface of interest. The replicating material is used to create an inverted replica of the microstructure of the second surface. Lengths of the cracks replicated on the replicating material are measured in order to determine the depth of intergranular attack on the surface of the part. In some embodiments, a fixture device may be attached on either side or both sides of the second surface of the part. The fixture device is configured to maintain an edge of the second surface so that the replicating material is able to cover an edge of the second surface and remain essentially flat.

BRIEF DESCRIPTION OF THE DRAWINGS

As shown in FIG. 2, a fixture device has been attached to the extension plate to aid in the replication process.

DETAILED DESCRIPTION

Figure 1A:
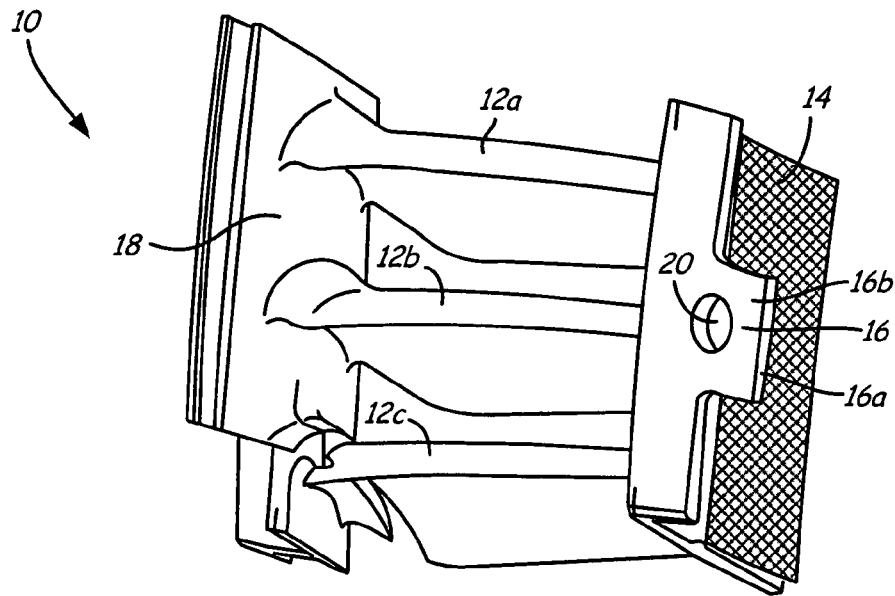
FIG. 1A is a perspective view of a vane assembly for use in a gas turbine engine.
Figure 1B:
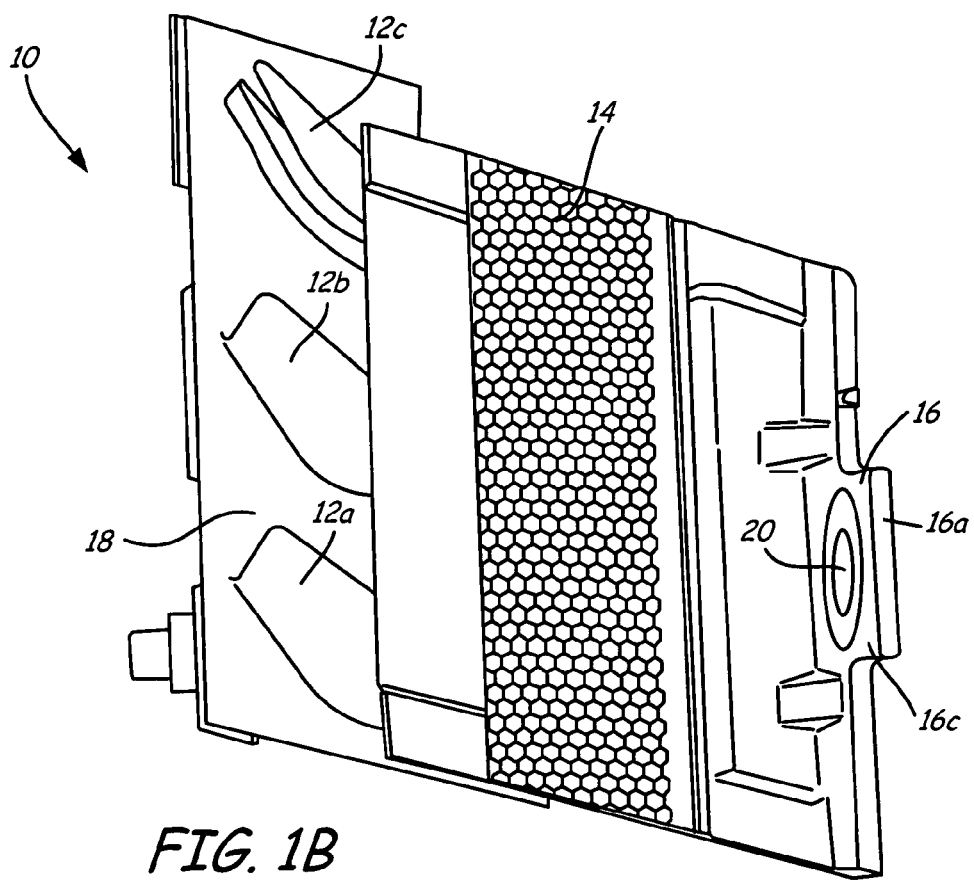
FIG. 1B is a perspective view of the vane assembly of FIG. 1A rotated approximately 180 degrees. The vane assembly includes an extension plate configured for attaching the vane assembly to a case of the engine.

FIGS. 1A and 1B are perspective views of vane assembly 10, which may be part of a low pressure turbine or a high pressure turbine, both of a gas turbine engine. Vane assembly 10 may be formed by casting of a metal alloy, such as, for example, a nickel alloy. As shown in FIG. 1A, vane assembly 10 includes three vanes 12a, 12b, and 12c, top platform 14, extension plate 16, and bottom platform 18. Extension plate 16 is configured for attaching vane assembly 10 to a case of the engine and includes weld buttress hole 20.

During operation of the engine, vanes 12a, 12b, and 12c may develop cracks. Other portions of vane assembly 10 may also develop cracking. As such, vane assembly 10 may be removed from the engine to repair the cracks. A repair process, such as Turbofix®, or similar methods of activated diffusion bonding, may be used to repair the cracks. Prior to performing the repair, vane assembly 10 is normally cleaned with hydrogen fluoride, or a comparable material, in order to clean the surfaces of the cracks. However, this cleaning agent is aggressive and corrosive, attacking a base metal of vane assembly 10. This intergranular attack (IGA) of the base metal results in cracks that may impair an operational life of vane assembly 10, particularly vanes 12a, 12b, and 12c. As such, it is necessary to measure a depth of the intergranular attack to determine if the part is still repairable.

In order to measure a depth of IGA in vanes 12a, 12b, and 12c, it is common to remove a sample of material from one of vanes 12a, 12b or 12c in order to form a micro (i.e. a metal sample). The micro is then placed under a microscope in order to view the microstructure of the micro and measure the depth of IGA. A disadvantage of this technique is that the micro is cut out of one of vanes 12a, 12b or 12c, and the removed material needs to be reinserted or replaced after determining the IGA depth. In either case, to insert the material into the vane, whether it is the original micro or a replacement piece of metal, it must be welded and heat treated. This destructive method for measuring IGA depth is time consuming and costly.

A non-destructive method of measuring IGA depth is described herein. A replicating material may be placed on a surface of vane assembly 10 to create an inverted replica of the microstructure. As shown below, this method yields the same results as compared to if a piece is removed from assembly 10 to create a micro. The replicating material is placed on a surface that is transverse or approximately 90 degrees to a surface that has been cleaned with hydrogen fluoride. Prior to applying the replicating material to the surface, the surface may be polished and etched. Since these processes may remove some material from the surface, although minimal, a non-critical surface of vane assembly 10 is typically chosen for replication. In preferred embodiments, an essentially flat surface is selected for replication.

In an exemplary embodiment, a surface of extension plate 16 may be used as a replication surface. This is described in detail below, with reference to FIGS. 2 through 5. It is recognized that other surfaces of vane assembly 10 may also be used as a replication surface, such as a side of top platform 14. Determining IGA on one or more of the surfaces of extension plate 16 is representative of IGA on other portions of vane assembly 10, including vanes 12, assuming the other portions of assembly 10 underwent the same hydrogen fluoride cleaning process. In an exemplary embodiment shown in FIGS. 2-5, a fixture device may be used for maintaining at least one of the edges on the replication surface. It is recognized that the fixture device is not required to perform the method described herein. However, as explained below, the fixture device aids in the process of creating an accurate replica on the replicating material.

As shown in FIGS. 1A and 1B, extension plate 16 includes top surface 16a, first side surface 16b, and second side surface 16c. A first step in the method for measuring IGA is to determine which surface of extension plate 16 is to be replicated. Commonly, all surfaces of extension plate 16 were cleaned with hydrogen fluoride. Top surface 16a may be arbitrarily chosen as the replication surface. Top surface 16a is essentially 90 degrees to first and second side surfaces 16b and 16c; thus, top surface 16a may be used to determine a depth of IGA in side surfaces 16b and 16c.

Figure 2:
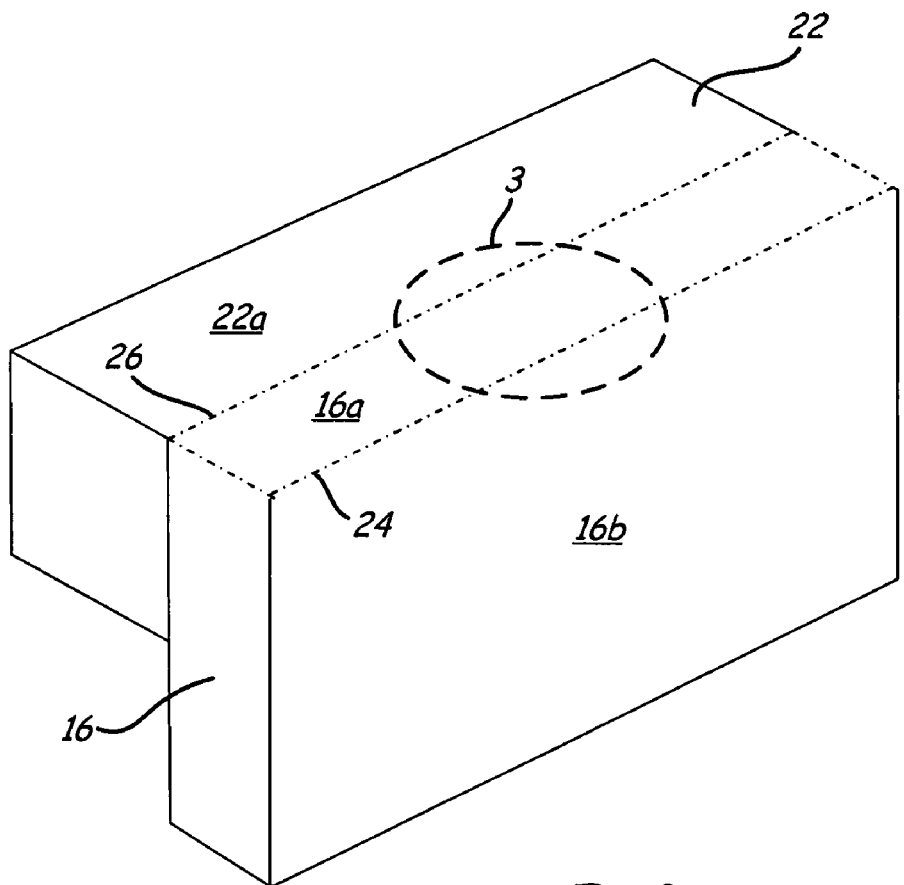
FIG. 2 is an expanded view of a portion of the extension plate of the vane assembly of FIGS. 1A and 1B.

FIG. 2 is a schematic of an expanded portion of extension plate 16 of assembly 10, as shown in FIGS. 1A and 1B, with fixture device 22 shown attached to extension plate 16. After choosing a replication surface (i.e. top surface 16a), a next step is to attach fixture device 22 to extension plate 16 such that surface 22a of fixture device 22 is adjacent to top surface 16a. Fixture device 22 is configured as an edge retention device. In an exemplary embodiment, fixture device 22 is formed from epoxy.

Top surface 16a includes first edge 24, defined as an intersection of top surface 16a and first side surface 16b, and second edge 26, defined as an intersection of top surface 16a and second side surface 16c (not shown in FIG. 2). Although not labeled in FIG. 2, top surface 16a includes two additional edges where top surface 16a intersects with end surfaces of extension plate 16.

Figure 3:
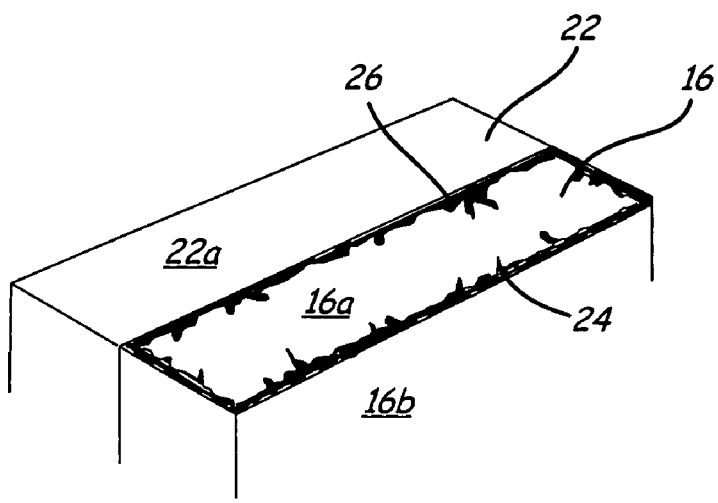
FIG. 3 is an expanded view of a portion 3 of the extension plate of FIG. 2.

FIG. 3 is a schematic of an expanded portion 3 of plate 16 of FIG. 2 to illustrate a formation of intergranular attack in the metal of extension plate 16. Intergranular attack is a surface phenomenon such that the attack or corrosion starts at the surface of the metal that the hydrogen fluoride or other corrosive agent is applied to and works its way further down into the metal. Cracks shown on top surface 16a near first edge 24 are cracks that are formed into first side surface 16b; similarly cracks shown near second edge 26 are cracks that are formed into second side surface 16c (not shown). Thus, in order to determine a depth of IGA in first side surface 16b and second side surface 16c, replication of surface 16a includes replication up to edges 24 and 26. Fixture device 22 is used to maintain edge 26, as discussed in more detail below.

Figure 4:
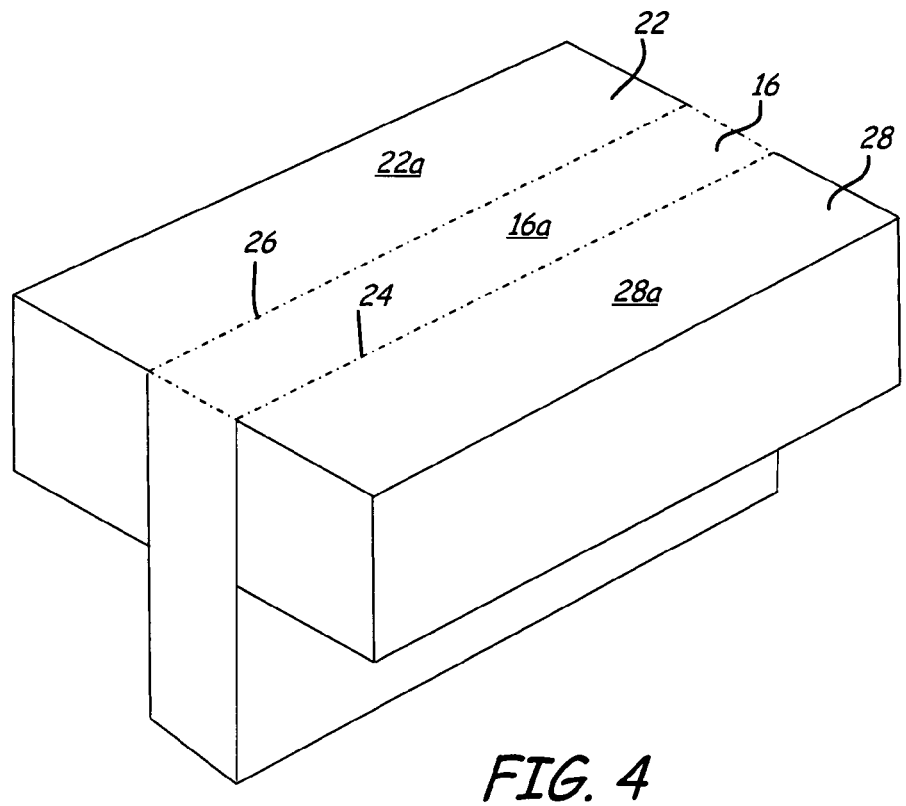
FIG. 4 shows the extension plate of FIG. 2 after a second fixture device has been attached to it.

FIG. 4 illustrates a next step in which second fixture device 28 is attached to extension plate 16, such that plate 16 is sandwiched between fixture device 22 and second fixture device 28. Surface 28a of fixture device 28 is adjacent to surface 16a of extension plate 16. Fixture device 28 is similar to fixture device 22 and is used to maintain first edge 24. Fixture devices 22 and 28 are temporarily attached to extension plate 16 through known attachment means, including, but not limited to, temporary bonding with adhesive.

Once fixture devices 22 and 28 are attached to extension plate 16, the replication surface (top surface 16a) is ground and polished to create a smooth surface. In most cases, a minimal amount of material is removed from surface 16a. The specifics of the process depend on a roughness of surface 16a. For example, in some cases, the process begins with 80 grit aluminum oxide paper; and in other instances, if surface 16a is fairly smooth, the process begins with 240 grit paper. Next, surface 16a is polished using, for example, diamond paste and a lubricant solution, such as Varsol. After polishing, surface 16a is then cleaned with acetone, followed by chemical etching. The etching process is performed on surface 16a to remove a top layer of the metal so that a microstructure of surface 16a is visible.

The surface preparation and cleaning steps described above may also be performed on surfaces 22a and 28a of fixture devices 22 and 28. It is recognized that preparation and cleaning of surface 16a may be achieved through known alternative techniques.

At this stage, the replicating material may be placed on surface 16a to create an inverted replica of the microstructure of surface 16a. In an exemplary embodiment, the replicating material is cellulose acetate. Another suitable replicating material includes, but is not limited to, collodion, which is a nitrocellulose solution (also known as proxylin solution). It is recognized that other materials capable of creating a replica of the microstructure of the metal may be used in the method described herein.

Figure 5:
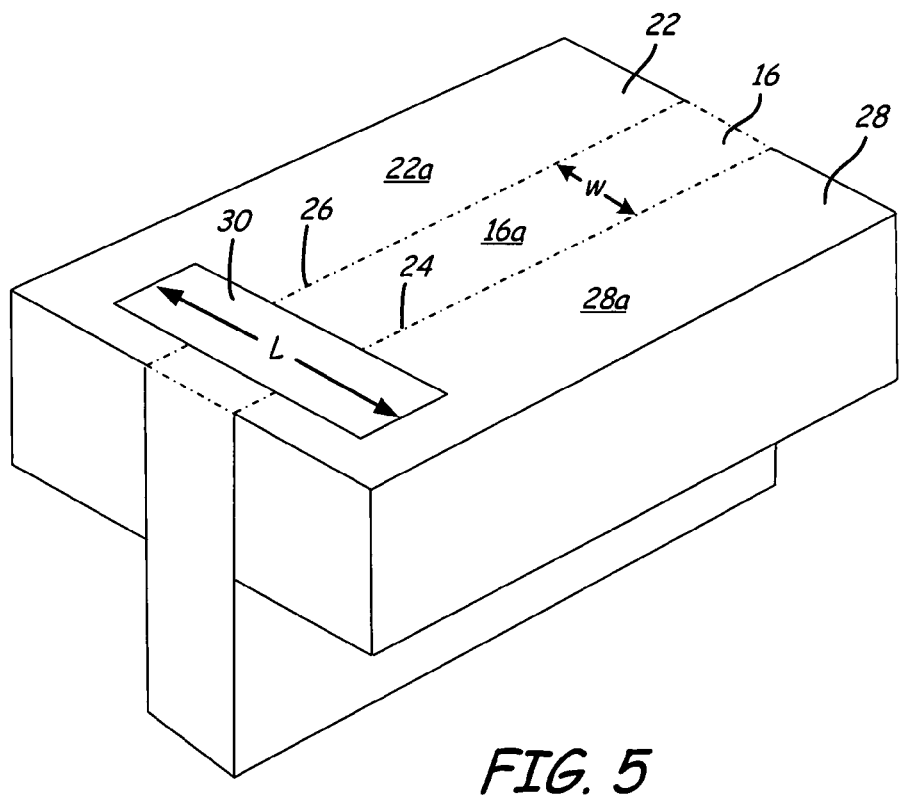
FIG. 5 illustrates placement of a replicating material on a surface of the extension plate to create a replica of a microstructure of the surface.

FIG. 5 shows replicating material 30 attached to surface 16a of plate 16 and surfaces 22a and 28a of fixture devices 22 and 28. In the exemplary embodiment shown in FIG. 5, replicating material 30 covers an entire width W of surface 16a, as well as a portion of surfaces 22a and 28a. Dimensions of material 30 may vary so long as length L of material 30 is greater than width W of surface 16a, yet material 30 is small enough to fit on a slide of a microscope. If length L of material 30 is greater than width W of surface 16a, an inverted replica created by material 30 includes a microstructure at both edges 24 and 26. In that case, the inverted replica shows IGA for both side surfaces 16b and 16c of extension plate 16. In other embodiments, length L of material 30 may be less than width W of surface 16a. In that case, one portion of material 30 may overlap one of either first edge 24 or second edge 26 such that it is possible to measure IGA for either first side surface 16b or second side surface 16c.

In an exemplary embodiment, replicating material 30 is a cellulose acetate film. To attach replicating material 30 to surfaces 16a, 22a, and 28a, acetone is first applied to surfaces 16a, 22a, and 28a. In an exemplary embodiment a reagent grade acetone is used. A sufficient amount of time is permitted to allow the acetone to dry on surfaces 16a, 22a, and 28a.

Replicating material 30 may be applied to surfaces 16a, 22a, and 28a using a pair of tweezers or an equivalent device. Immediately before applying material 30, acetone may be applied a second time to surfaces 16a, 22a, and 28a. Once replicating material 30 is placed on surfaces 16a, 22a, and 28a, material 30 is left on for a sufficient amount of time for material 30 to dry. The time may vary depending on a thickness of material 30. An appropriate time range may be between three and ten minutes.

Replicating material 30 may then be peeled off of surfaces 16a, 22a, and 28a. (The tweezers may also be used during this removal step.) Material 30 is then placed on a glass slide which may be placed under a microscope. Material 30 is oriented on the slide such that a side of material 30 that contacted surfaces 16a, 22a, and 28a is oriented facing up on the slide. In some embodiments, scotch tape may be used near corners of replicating material 30 to hold material 30 down on the slide.

A magnified photograph of replicating material 30 is then taken in order to view the microstructure of surface 16a and determine a depth of IGA in side surfaces 16b or 16c. In some embodiments, material 30 may be chrome coated or sputtered in order to provide better resolution of the microstructure of surface 16a; however, this step is not required. The measured depth of IGA in side surfaces 16b and/or 16c is indicative of IGA in other parts of vane assembly 10 (see FIGS. 1A and 1B). Based on the measurements from replicating material 30, a decision may be made as to whether vane assembly 10 may continue operation within the engine.

As stated above, fixture devices 22 and 28 are not required in the replication method described herein. However, without fixtures 22 and 28, it may be difficult to create a replica on replicating material 30 that includes a microstructure of the metal at edges 24 and 26 of surface 16a. For example, without fixture 22, if material 30, having length L as shown in FIG. 5, is placed on surface 16a, material 30 may wrap around edge 26 and onto side surface 16c. Once the acetone dries, material 30 may become brittle, and material 30 may crack at or around edge 26 when it is time to remove material 30 from surface 16a (and 16c). At the same time, material 30 should be of sufficient length so that it is applied right to edge 26 (in order to accurately determine a length of the cracks formed through surface 16c). Fixture device 22 is used so that material 30 covers edge 26, while remaining flat. Replicating material 30 may then easily be peeled off of surfaces 22a and 16a after it is dry. It is recognized that the method described herein may include alternative devices for edge retention.

In an alternative embodiment, replicating material 30 is collodion, which is applied as a liquid to surface 16a. The liquid dries on surface 16a to form a film that may then be peeled off of surface 16a. As described above, fixture devices 22 and 28 may be used to maintain edges 24 and 26. In that case, the liquid may also be applied to surfaces 22a and 28a such that a film forms across surfaces 16a, 22a and 28a.

Figure 6:
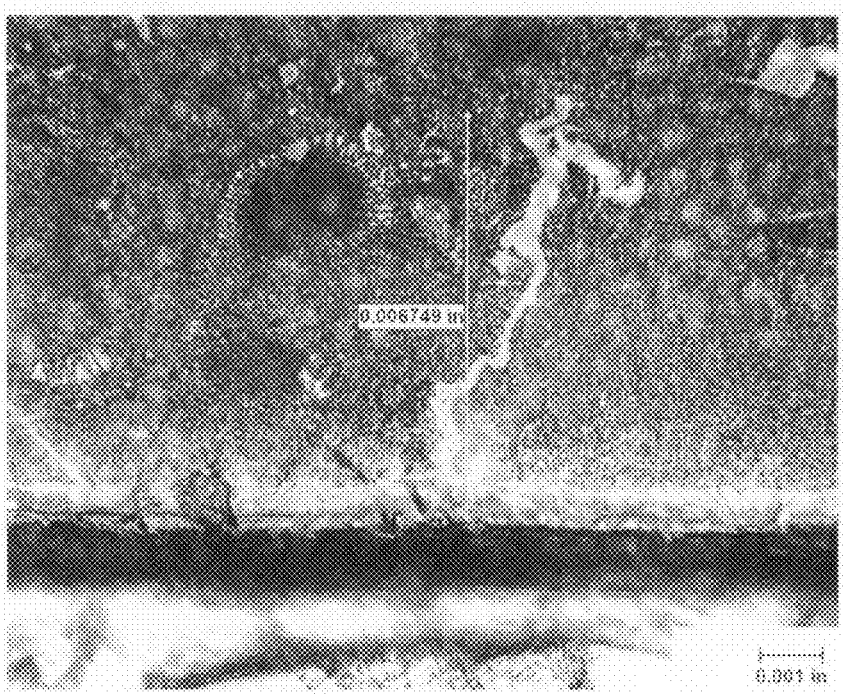
FIGS. 6 and 7 are magnified photographs comparing a microstructure for a micro or sample that is removed from a metal part and a replicated microstructure formed on a replicating material.
Figure 7:
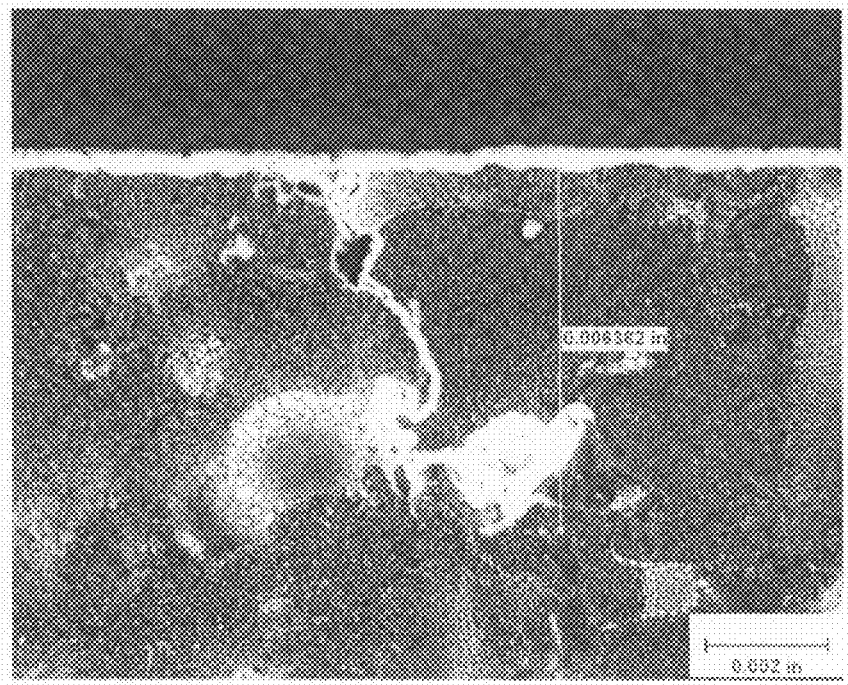

FIG. 6 is a photograph of a replica, created using the process described above, compared to an actual metal sample, as shown in FIG. 7. The replicating material used in FIG. 6 is cellulose acetate. FIGS. 6 and 7 both are magnified 200 times. As illustrated by FIGS. 6 and 7, the acetate replica shows an inverted image of the actual sample, but a microstructure of the metal in both photographs is essentially identical.

As described above, to measure a depth of IGA in a surface, a micro or a replica is taken of a surface that is transverse or 90 degrees to the surface of interest. The photographs in FIGS. 6 and 7 are for a surface similar to surface 16a of FIGS. 2-5. The most prominent crack shown in FIGS. 6 and 7 represents a depth of attack in a surface that is transverse to surface 16a. In FIG. 6, the depth of the crack is 0.006749 inches (0.1714 mm), whereas in FIG. 7 the depth of the crack is 0.006382 inches (0.1621 mm). The difference in numbers is negligible and validates that the replication technique described above provides equivalent data without requiring that a micro be made from the metal part.

Figure 8:
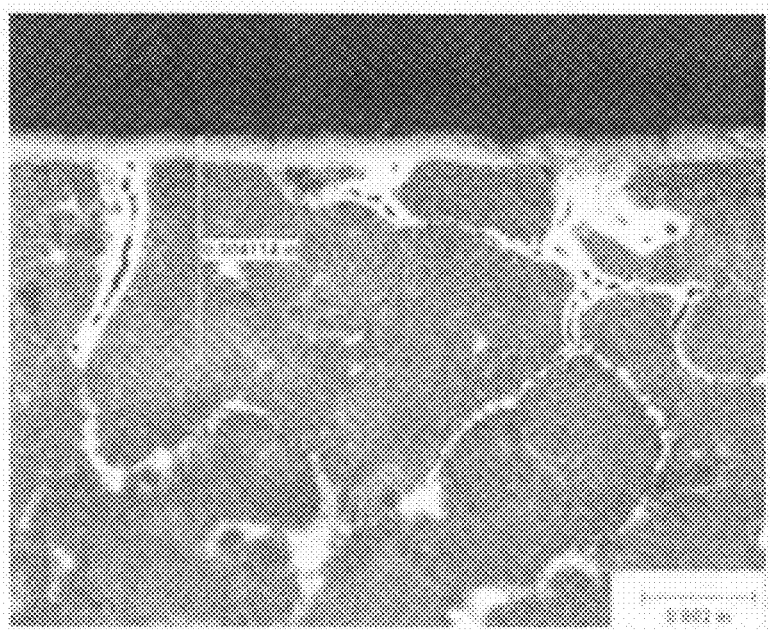
FIGS. 8 and 9 are a similar set of photographs comparing a microstructure for a metal micro to a replicated microstructure.
Figure 9:
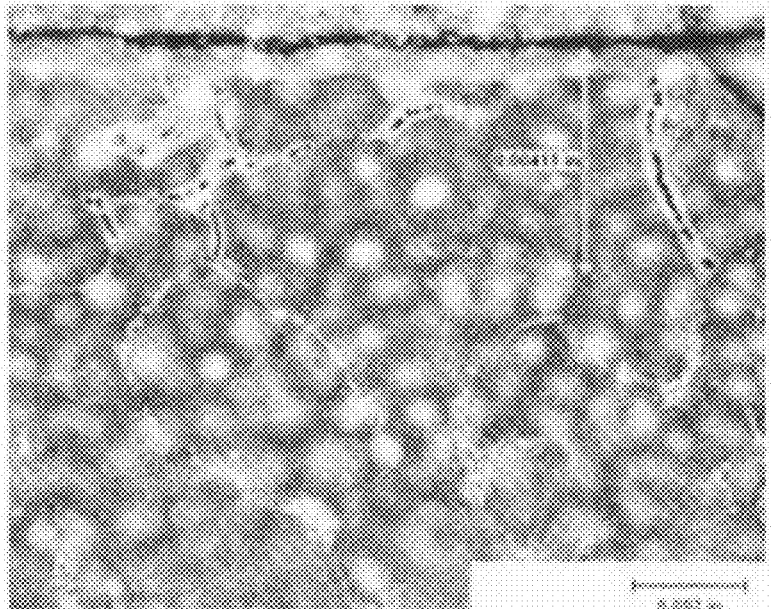

FIGS. 8 and 9 are similar to FIGS. 6 and 7, further illustrating that the non-destructive replication technique provides the same data to measure IGA, as compared to data from a metal micro removed from the part. FIG. 8 is a photograph (magnified 200 times) of an actual micro, showing an IGA depth of 0.004114 inches (0.1045 mm). FIG. 9 is a photograph (magnified 200 times) of an acetate replica with an IGA depth of 0.00411 inches (0.1044 mm). FIGS. 8 and 9 further confirm that placing a piece of cellulose acetate on a metal surface provides an accurate replica of the microstructure of the surface.

This method of using a replicating material to create a replica of a metal surface is described in the context of a vane assembly of a low pressure turbine or a high pressure turbine of an aircraft engine. It is recognized that this method may be used for other metal parts, such as other parts within an aircraft engine, including turbine blades or a blade assembly, or many other types of non-aero metal parts.

Although the present invention has been described with reference to preferred embodiments, workers skilled in the art will recognize that changes may be made in form and detail without departing from the spirit and scope of the invention.

The invention claimed is:

1. A method of determining a depth of intergranular attack on a first surface of a metal part, the method comprising:
    placing a replicating material on a second surface of the part to create an inverted replica of a microstructure of the second surface, wherein the second surface of the part is essentially perpendicular to and intersects with the first surface;
    removing the replicating material from the second surface of the part; and
    measuring a length of a crack replicated on the replicating material to determine a depth of intergranular attack on the first surface of the part.

2. The method of claim 1 wherein the replicating material is cellulose acetate.

3. The method of claim 1 wherein the replicating material is collodion.

4. The method of claim 1 further comprising:
    applying a chrome coating to the replicating material after removing the replicating material from the second surface.

5. The method of claim 1 wherein measuring the length of a crack replicated on the replicating material includes placing the replicating material under a microscope.

6. The method of claim 1 wherein the part is a component of a gas turbine engine.

7. The method of claim 1 wherein the part includes at least one of a turbine vane assembly or a blade assembly of a gas turbine engine.

8. The method of claim 1 further comprising:
    preparing the second surface of the part prior to placing the replicating material on the second surface.

9. The method of claim 8 wherein preparing the second surface of the part includes polishing the second surface using at least one grit paper.

10. The method of claim 8 wherein preparing the second surface of the part includes applying acetone to the second surface.

11. The method of claim 8 wherein preparing the second surface of the part includes chemically etching the second surface.

12. The method of claim 1 further comprising:
    attaching a first fixture device to the part prior to placing the replicating material on the second surface, such that the first fixture device is configured to provide edge retention for a first edge defined as an intersection between the first surface and the second surface.

13. The method of claim 12 wherein the second surface of the part is essentially perpendicular to and intersects with a third surface, and the method further comprises:
    attaching a second fixture device to the part prior to placing the replicating material on the second surface, such that the part is sandwiched between the first fixture device and the second fixture device, and the second fixture device is configured to provide edge retention for a second edge defined as an intersection between the first surface and the third surface.

14. A method of creating an inverted replica of a microstructure of a cast metal alloy part used in a gas turbine engine, the method comprising:
preparing a second surface of the part, wherein the second surface of the part is approximately 90 degrees relative to a first surface of the part and intersects with the first surface;
placing a replicating material on the second surface of the part;
leaving the replicating material on the second surface of the part for a time sufficient to create an inverted replica of a microstructure of the second surface on the replicating material;
peeling the replicating material off of the second surface; and
measuring a replicated crack in the microstructure on the replicating material to determine a depth of intergranular attack on the first surface.

15. The method of claim 14 wherein the replicating material includes at least one of cellulose acetate and collodion.

16. The method of claim 14 wherein the part includes at least one of a turbine vane for an aircraft engine or a blade for an aircraft engine.

17. The method of claim 14 wherein the metal alloy is a nickel alloy.

18. The method of claim 14 wherein preparing the second surface includes at least one of grinding, polishing, etching, and applying acetone.

19. The method of claim 14 wherein measuring a replicated crack in the microstructure on the replicating material includes magnifying the microstructure by placing the replicating material under a microscope.

20. The method of claim 14 further comprising:
attaching a first edge retention device to the first surface of the metal alloy part, prior to placing the replicating material on the second surface, such that the first edge retention device is configured to provide edge retention for a first edge defined as an intersection between the first surface and the second surface.

21. The method of claim 20 wherein the replicating material is placed on the second surface of the part and on the first edge retention device.

22. The method of claim 20 further comprising:
attaching a second edge retention device to a third surface of the part, prior to placing the replicating material on the second surface, wherein the third surface of the part is approximately 90 degrees relative to the second surface of the part and intersects with the second surface, and the second edge retention device is configured to provide edge retention for a second edge defined as an intersection between the second surface and the third surface.

23. The method of claim 22 wherein the replicating material is placed on the second surface of the part and on the first and second edge retention devices.

24. The method of claim 22 further comprising:
measuring a second replicated crack on the replicating material to determine a depth of intergranular attack on the third surface of the part.

25. A method of determining a depth of intergranular attack on a metal alloy, the method comprising:
treating a surface of the metal alloy to remove a top layer thereof;
cleaning the surface of the metal alloy;
applying a replicating material to the surface of the metal alloy for a time sufficient to create a replica of a microstructure of the metal alloy on the replicating material; and
magnifying an image of the replica on the replicating material to determine a depth of intergranular attack in the metal alloy.

26. The method of claim 25 wherein the replicating material includes at least one of cellulose acetate and collodion.

27. The method of claim 25 wherein the metal alloy is a nickel alloy.

28. The method of claim 25 wherein treating the surface of the fixture device includes at least one of grinding, polishing, and chemical etching.

29. The method of claim 25 wherein the metal alloy includes at least one of a turbine vane assembly and a turbine blade assembly.

30. The method of claim 25 further comprising:
attaching a fixture device to a portion of the metal alloy; and
applying the replicating material to a surface of the fixture device located adjacent to the surface of the metal alloy.

31. The method of claim 30 wherein the fixture device is formed from epoxy.

32. The method of claim 30 further comprising:
attaching a second fixture device to the portion of the metal alloy such that the portion of the metal alloy is sandwiched between the first and second fixture devices; and
applying the replicating material to a surface of the second fixture device located adjacent to the surface of the metal alloy.

* * * * *